United States Patent
Huang (10) Patent No.: US 9,781,243 B1
(45) Date of Patent: Oct. 3, 2017

(54) OPTIMIZING WEARABLE DEVICE SETTINGS USING MACHINE LEARNING

(71) Applicant: Intel Corporation, Santa Clara, CA (US)

(72) Inventor: Jinshi James Huang, Fremont, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/193,944

(22) Filed: Jun. 27, 2016

(51) Int. Cl.
*H04W 4/04* (2009.01)
*H04M 1/725* (2006.01)
(Continued)

(52) U.S. Cl.
CPC ........ *H04M 1/72527* (2013.01); *G06F 1/163* (2013.01); *G06N 99/005* (2013.01);
(Continued)

(58) Field of Classification Search
CPC .. H01M 1/72527; G06F 1/163; G06F 3/1423; G06F 19/322; G06N 99/005;
(Continued)

(56) References Cited

U.S. PATENT DOCUMENTS

| 9,223,494 B1 | 12/2015 | Desalvo | |
| 2014/0070957 A1* | 3/2014 | Longinotti-Buitoni | G06F 1/163 340/870.01 |

(Continued)

FOREIGN PATENT DOCUMENTS

| WO | WO-2014085910 A1 | 6/2014 |
| WO | 2015085326 A1 | 6/2015 |

(Continued)

OTHER PUBLICATIONS

"Disability Innovations: Talkitt app helps disabled people use their voice", Voiceitt, Help and information, [Online]. Retrieved from the Internet: <URL: https://blog.scope.org.uk/2015/06/25/disability-innovations-talkitt-app-helps-disabled-people-use-their-voice/>, (Jun. 25, 2015), 4 pgs.

(Continued)

*Primary Examiner* — Thanh Le
(74) *Attorney, Agent, or Firm* — Schwegman Lundberg & Woessner, P.A.

(57) ABSTRACT

Techniques for optimizing wearable device settings using machine learning are described. A mobile device may receive, from a wearable device (such as a wristwatch), sensor data corresponding to a reaction of a user wearing the wearable device to an output modality produced by the wearable device. The mobile device may solicit user feedback for the output modality produced by the wearable device. The mobile device may receive, via a sensor set, user feedback data corresponding to a user feedback for the output modality. The mobile device may upload the sensor data and the user feedback data to a cloud-based application. The mobile device may receive a knowledge package, including a classification algorithm trained using the sensor data and the user feedback data, from the cloud-based application. Finally, the mobile device may send the knowledge package to the wearable device.

24 Claims, 9 Drawing Sheets

(51) Int. Cl.
*H04B 1/3827* (2015.01)
*H04W 4/00* (2009.01)
*G06F 1/16* (2006.01)
*G06N 99/00* (2010.01)

(52) U.S. Cl.
CPC ............ *H04B 1/385* (2013.01); *H04W 4/001* (2013.01); *H04W 4/005* (2013.01)

(58) Field of Classification Search
CPC ...... H04B 1/385; H04W 4/001; H04W 4/005; H04W 12/08; H04W 12/06; G09G 5/006; G09G 5/395; G06T 1/60
See application file for complete search history.

(56) References Cited

U.S. PATENT DOCUMENTS

| | | | |
|---|---|---|---|
| 2014/0164750 A1 | 6/2014 | Tang et al. | |
| 2014/0223421 A1 | 8/2014 | Carter et al. | |
| 2015/0133191 A1 | 5/2015 | Raman | |
| 2015/0180716 A1 | 6/2015 | Aminzade | |
| 2015/0278449 A1* | 10/2015 | LaBorde | G06F 19/322 705/3 |
| 2015/0332031 A1* | 11/2015 | Mistry | G06F 21/316 726/19 |
| 2016/0070441 A1* | 3/2016 | Paek | G06F 3/0482 715/773 |
| 2016/0232131 A1* | 8/2016 | Liu | G06F 17/211 |

FOREIGN PATENT DOCUMENTS

WO   WO-2015127062 A1   8/2015
WO   WO-2015127441 A1   8/2015

OTHER PUBLICATIONS

"Overview: Wearable Device Software Management", Harman International, [Online]. Retrieved from the Internet: <URL: http://www.redbend.com/en/solutions/iot/wearable-device-software-management/overview>, (Feb. 15, 2015), 1 pgs.

"International Application No. PCT/US2017/026785, International Search Report dated Jul. 21 2017", 4 pages.

"International Application Serial No. PCT/US2017/026785, Written Opinion dated Jul. 21 2017", 10 pages.

* cited by examiner

OPTIMIZING WEARABLE DEVICE SETTINGS USING MACHINE LEARNING

TECHNICAL FIELD

The present disclosure relates generally to wearable devices, and specifically to optimizing wearable device settings using machine learning.

BACKGROUND

The human senses provide information from various modalities vision (sight), audition (hearing), tactile (touch), olfactory (smell), taste, proprioception (the sense of the relative position of neighboring parts of the body and strength of effort being employed in movement), and the vestibular system (which contributes to the sense of balance and spatial orientation for the purpose of coordinating movement with balance)—that humans use to function. Wearable devices may produce outputs of various modalities with a wide range of settings.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments or examples discussed in the present document.

DETAILED DESCRIPTION

The present disclosure describes methods, systems, and computer program products that individually facilitate optimizing wearable device settings using machine learning. In the following detailed description, for purposes of explanation, numerous specific details are set forth in order to provide a thorough understanding of the various aspects of the presently disclosed subject matter. However, it will be evident to those skilled in the art, after reading and understanding the present subject matter, that the presently disclosed subject matter may be practiced without these specific details. In other instances, well-known methods, procedures, and components have not been described in detail so as not to obscure the presently disclosed subject matter.

Wearable devices, such as smartwatches, are becoming increasingly ubiquitous. Wearable devices may produce a variety of environmental stimuli, such as light, sound, vibration, etc. Although a wearable device may have user-configurable settings to control one or more of the environmental stimuli produced by the wearable device, a user of the wearable device may not know which setting configuration is optimal (or even acceptable) for the user. Disclosed embodiments improve the user experience for a user of a wearable device by using machine-learning techniques to optimize the settings of the wearable device.

Sensory processing disorder ("SPD"; also known as "sensory integration dysfunction") is a condition that exists when multisensory integration is not adequately processed in order to provide appropriate responses to the demands of the environment (e.g., the brain has trouble receiving and responding to information received by one or more senses). SPD is closely related to (and is often comorbid with) autism. Some people with SPD are oversensitive to environmental stimuli, while other people with SPD may be undersensitive to environmental stimuli.

SPD may be characterized by significant problems with organizing sensation(s) coming from the body and/or the environment and may manifested by difficulties in the performance in one or more of the main areas of life: productivity, leisure, play, or activities of daily living. People with SPD may experience a wide range of difficulties when processing input coming from a variety of senses, particularly tactile (e.g., finding fabrics itchy and hard to wear while others do not), vestibular (e.g., experiencing motion sickness while riding a car), and proprioceptive (e.g., having difficulty grading the force with which to hold a pen in order to write properly). The disclosed techniques may be useful for optimizing settings of a wearable device worn by a person having SPD.

Figure 1:
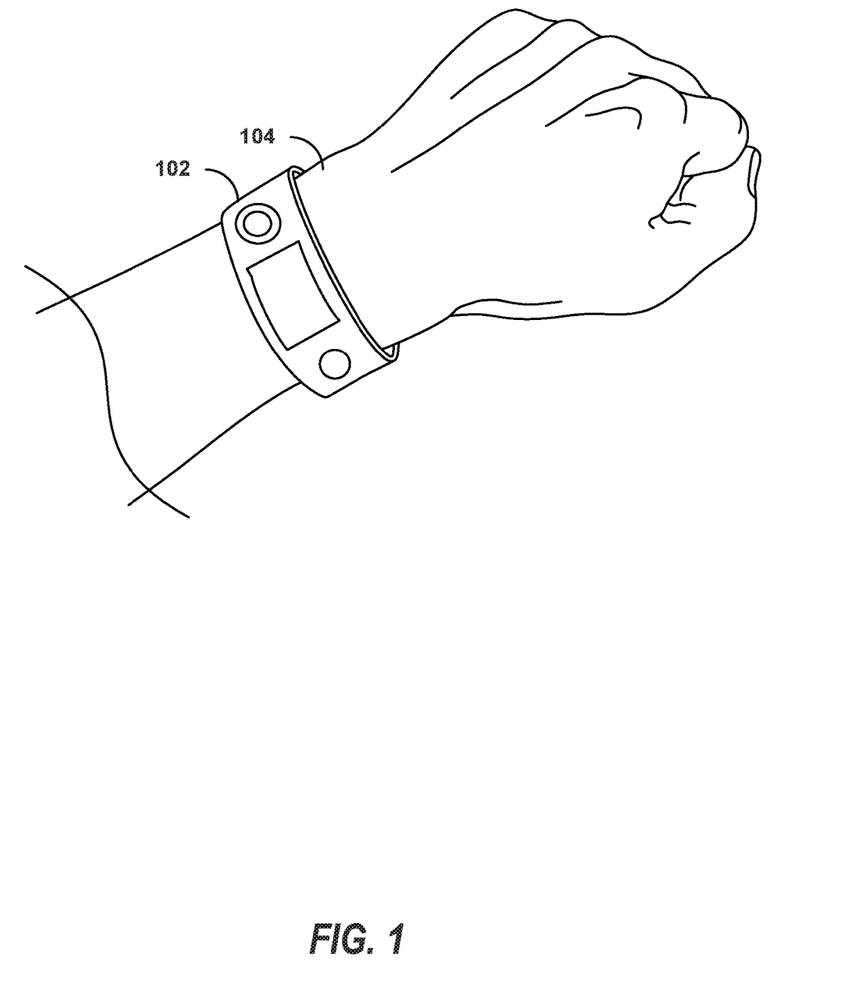
FIG. 1 illustrates a wearable device whose settings may be optimized using machine learning, according to an example embodiment.

FIG. 1 illustrates a wearable device 102 whose settings may be optimized using machine learning, according to an example embodiment. The wearable device 102 may be a watch worn on the wrist 104 of a user. Although FIG. 1 illustrates the wearable device 102 as a watch, in other embodiments, the wearable device 102 may be a necklace, a bracelet, an earring, eyeglasses, or any other form factor for an electronic device that may be worn by a user.

Figure 2:
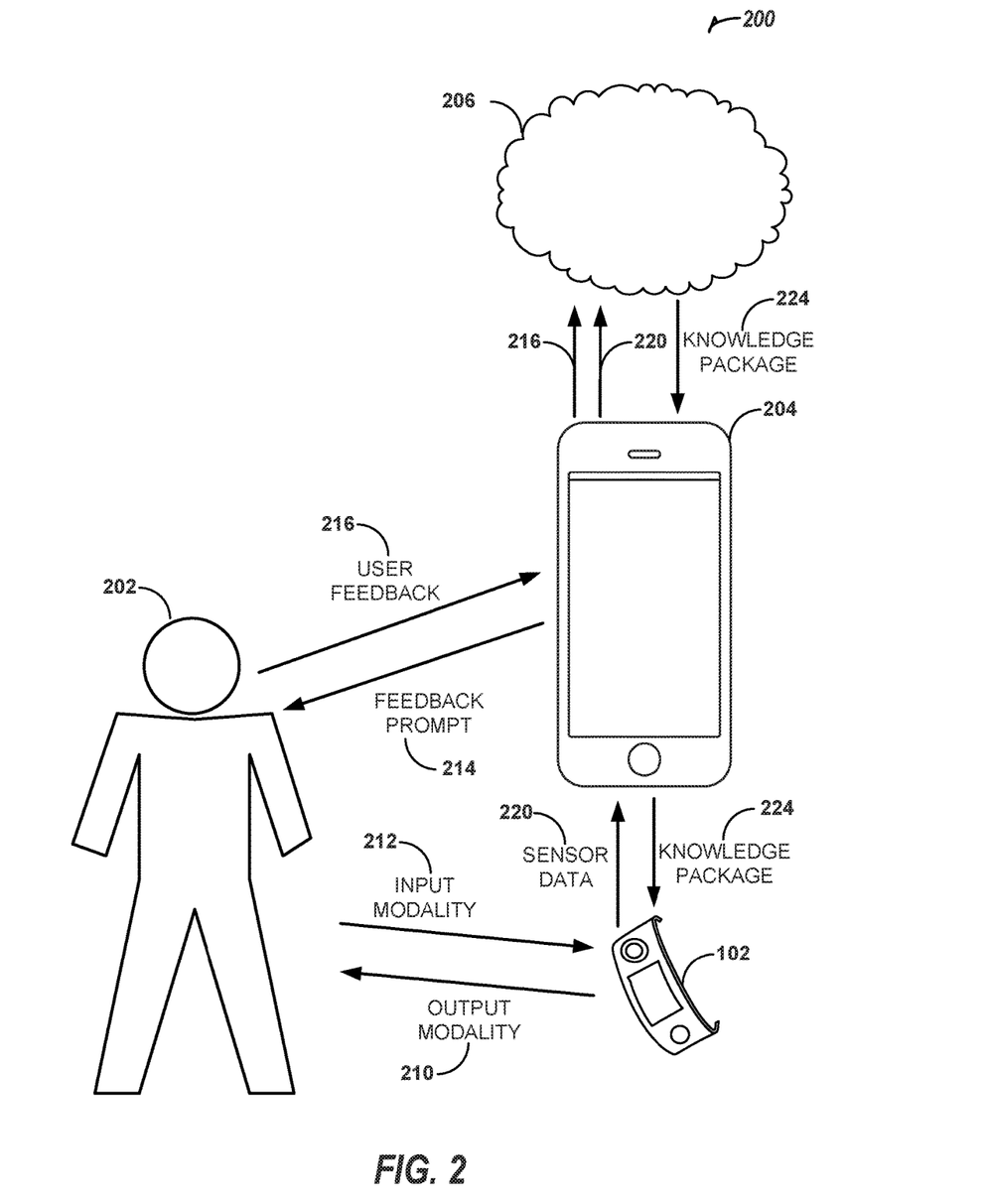
FIG. 2 illustrates a system for optimizing wearable device settings using machine learning, according to an example embodiment.

FIG. 2 illustrates a system 200 for optimizing wearable device settings using machine learning, according to an example embodiment. The system 200 includes the wearable device 102, a user 202 wearing the wearable device 102, and a cloud-based application 206 executing in a cloud-based platform (e.g., Microsoft® Azure™, Amazon Web Services, etc.). Optionally, in an embodiment, the system 200 includes a mobile device 204 such as a smartphone or a tablet computer. The user 202 in FIG. 2 is illustrated apart from the wearable device 102 for ease of illustration only; in typical usage, the wearable device 102 is worn by the user 202. As used in this document, an "output modality" is an output produced by a device that corresponds to and that may be perceived by a human using a human modality (e.g., sight, hearing, touch, smell, taste, proprioception, vestibular, etc.). Likewise, an "input modality" is an input produced by a human that corresponds to and that may be generated by a human modality.

Prior to typical usage by the user 202, the wearable device 102 may undergo a training process to optimize for the user 202 the settings of the wearable device's sensors and output modalities. During this training process, an application ("app") executing on the mobile device 204 may instruct the user 202 to perform one or more interactions, corresponding to one or more modalities, with the wearable device 102. An interaction may include the user 202 sensing one or more output modalities 210 generated by the wearable device 102 and/or the user 202 performing one or more input modalities 212 to the wearable device 102. Examples of an output modality 210 may include viewing light displayed on a display of the wearable device 102, listening to sound produced by a speaker of the wearable device 102, feeling a vibration generated by the wearable device 102, etc. Examples of an input modality 212 may include touching or pressing on a portion of the wearable device 102, speaking into a microphone of the wearable device 102, moving the wearable device 102 in a particular pattern or gesture, etc. The wearable device 102 may collect the user's reaction(s) to the one or more interactions using one or more sensors within the wearable device 102. The wearable device 102 may provide the collected sensor data 220 to the mobile device 204.

Many wearable devices 102 have limited user interfaces compared to those of smartphones and/or tablet computers; thus, although some user feedback 216 may be collected using only the wearable device 102, an app executing on a smartphone or tablet computer may be used to solicit feedback 216 regarding the interaction(s) from the user 202 that would be difficult for the user 202 to provide using only the wearable device 102. For example, the mobile device 204 may ask whether light displayed by a display of the wearable device 102 was too dim or too bright, whether sound produced by a speaker of the wearable device 102 was too quiet or too loud, whether vibrations generated by the wearable device 102 were too weak or too strong, etc. The user 202 may provide the user feedback 216 through one or more input mechanisms of the mobile device 204, including touch controls on the mobile device 204, aural input via a microphone of the mobile device 204, free-form text input on the mobile device 204, selection on the mobile device 204 of an emoji that best represents the user's reaction, etc. In an embodiment, the mobile device 204 may use a camera to monitor the expression(s) and/or behavior(s) of the user 202 in response to an interaction.

The mobile device 204 may provide the user feedback and sensor data 222 to the cloud-based application 206. The cloud-based application 206 may analyze the data 222, train a machine learning algorithm (e.g., a neural network) to execute on the wearable device 102, and generate a knowledge package 224 that includes the trained machine learning algorithm, program instructions, and the optimized device settings. The cloud-based application 206 may send the knowledge package 224 to the mobile device 204, which may then send the knowledge package 224 to the wearable device 102. Finally, the wearable device 102 may update itself by installing the knowledge package 224.

In embodiments that do not include the optional mobile device 204, the wearable device 102 may provide the feedback prompt(s) 214 to the user 202, may receive the user feedback 216 from the user 202, may provide the user feedback and sensor data 222 to the cloud-based application 206, and may receive the knowledge package 224 from the cloud-based application 206.

Figure 3:
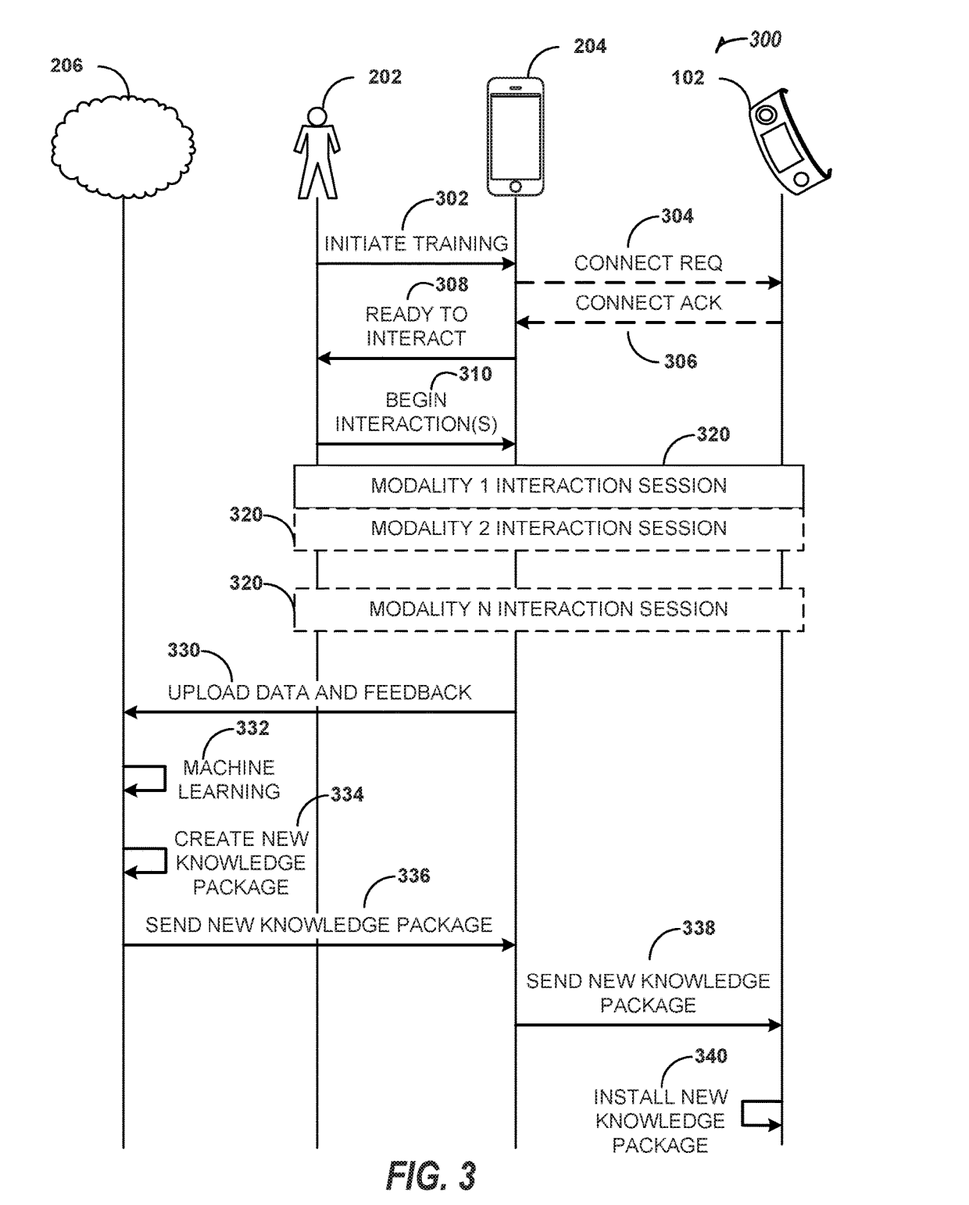
FIG. 3 illustrates a training process to optimize the settings of the wearable device using machine learning, according to an example embodiment.

FIG. 3 illustrates a training process 300 to optimize the settings of the wearable device 102 using machine learning, according to an example embodiment. The user 202 may initiate 302 the training process by providing an input to the mobile device 204. The initiate training 302 input may be launching a training app on the mobile device 204, pressing a button within the training app to indicate the user's desire to start training, etc.

If the mobile device 204 is not already connected to the wearable device 102, upon the mobile device 204 receiving the indication to initiate training, the mobile device 204 may connect to the wearable device 102. In an embodiment, the connection between mobile device 204 and wearable device 102 may include the mobile device 204 sending a connection request 304 to the wearable device 102 and the wearable device 102 sending a connection acknowledgement 306 to the mobile device 204.

Upon the mobile device 204 and the wearable device 102 being connected and ready to begin interactions, the mobile device 204 may inform the user 202 that the mobile device 204 and the wearable device 102 are ready to interact 308. The user 202 may then indicate 310 to the mobile device 204 that the mobile device 204 and the wearable device 102 are to begin interacting with the user 202.

The user 202 may interact with mobile device 204 and the wearable device 102 in a set of one or more modality interactions 320. Each modality interaction 320 may correspond to a modality of input and/or output of the wearable device 102, including sensor data sensed by the wearable device and user feedback received by the mobile device 204 and/or the wearable device 102. An example of a modality interaction 320 is illustrated and described in greater detail in FIG. 4.

The mobile device 204 may upload the sensor data and user feedback 330 received during one or more modality interactions 320 to the cloud-based application 206. The cloud-based application 206 may then train a machine learning algorithm (e.g., a neural network) 332 to optimize, based on the user feedback 216 and sensor data 220, the output modalities of the wearable device 102 for the user 202. The cloud-based application 206 may then create 334 a new knowledge package 224 that may include the trained machine learning algorithm, operating instructions, and the optimized device settings to be installed on the wearable device 102. The cloud-based application 206 may then send 336 the new knowledge package 224 to the mobile device 204.

The mobile device 204 may send 338 the new knowledge package 224 to the wearable device 102. The wearable device 102 may then install 340 the new knowledge package 224. In an embodiment, installing the new knowledge package 224 may include the mobile device 204 instructing the wearable device to reset itself. In an embodiment, optimization of the settings of the wearable device's sensors and output modalities may include multiple iterations of the training process 300.

Figure 4:
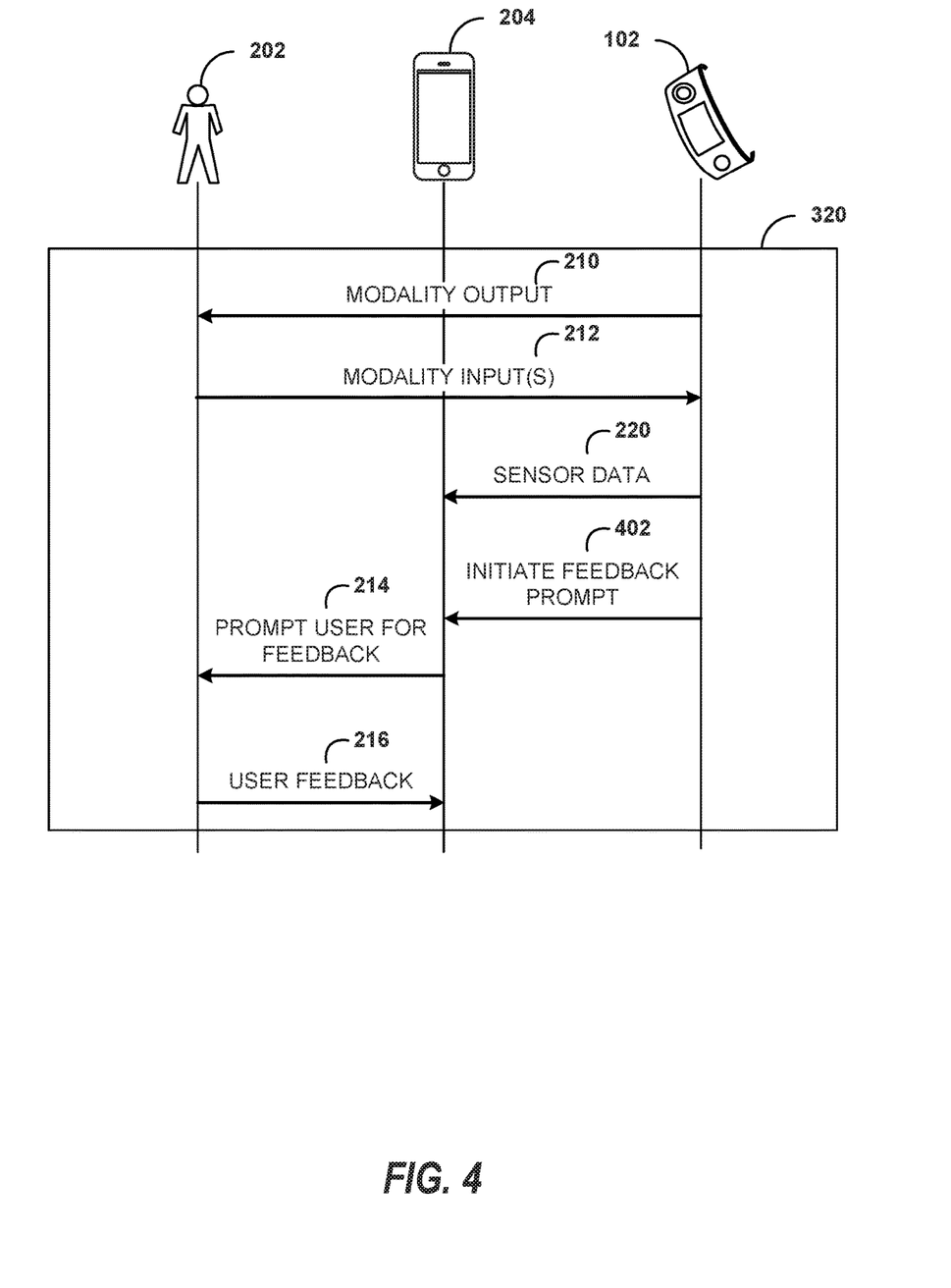
FIG. 4 illustrates a modality interaction session of the training process to optimize the settings of the wearable device using machine learning, according to an example embodiment.

FIG. 4 illustrates a modality interaction session 320 of the training process to optimize the settings of the wearable device using machine learning, according to an example embodiment. A modality interaction session 320 may include the user sensing one or more output modalities 210 generated by the wearable device 102 and/or the user performing one or more input modalities 212 to the wearable device 102. Examples of an output modality 210 may include viewing light displayed on a display of the wearable device 102, listening to sound produced by a speaker of the wearable device 102, feeling a vibration generated by the wearable device 102, etc. Examples of an input modality 212 may include touching or pressing on a portion of the wearable device 102, speaking into a microphone of the wearable device 102, moving the wearable device 102 in a particular pattern or gesture, etc.

During the modality interaction session 320, the wearable device 102 may collect data using one or more sensors within the wearable device 102. The wearable device 102 may provide the collected sensor data 220 to the mobile device 204.

The wearable device 102 may instruct 402 the app executing on the mobile device 204 to prompt the user 202 for feedback regarding one or more output modalities 210 and/or input modalities 212. For example, the mobile device 204 may ask whether light displayed by a display of the wearable device 102 was too dim or too bright, whether sound produced by a speaker of the wearable device 102 was too quiet or too loud, whether vibrations generated by the wearable device 102 were too weak or too strong, etc. The user 202 may provide the user feedback 216 through one or more input mechanisms, including touch controls on the mobile device 204, aural input via a microphone of the mobile device 204, etc. In an embodiment, the mobile device 204 may use a camera to monitor the expression(s) and/or behavior(s) of the user 202 in response to an interaction.

Figure 5:
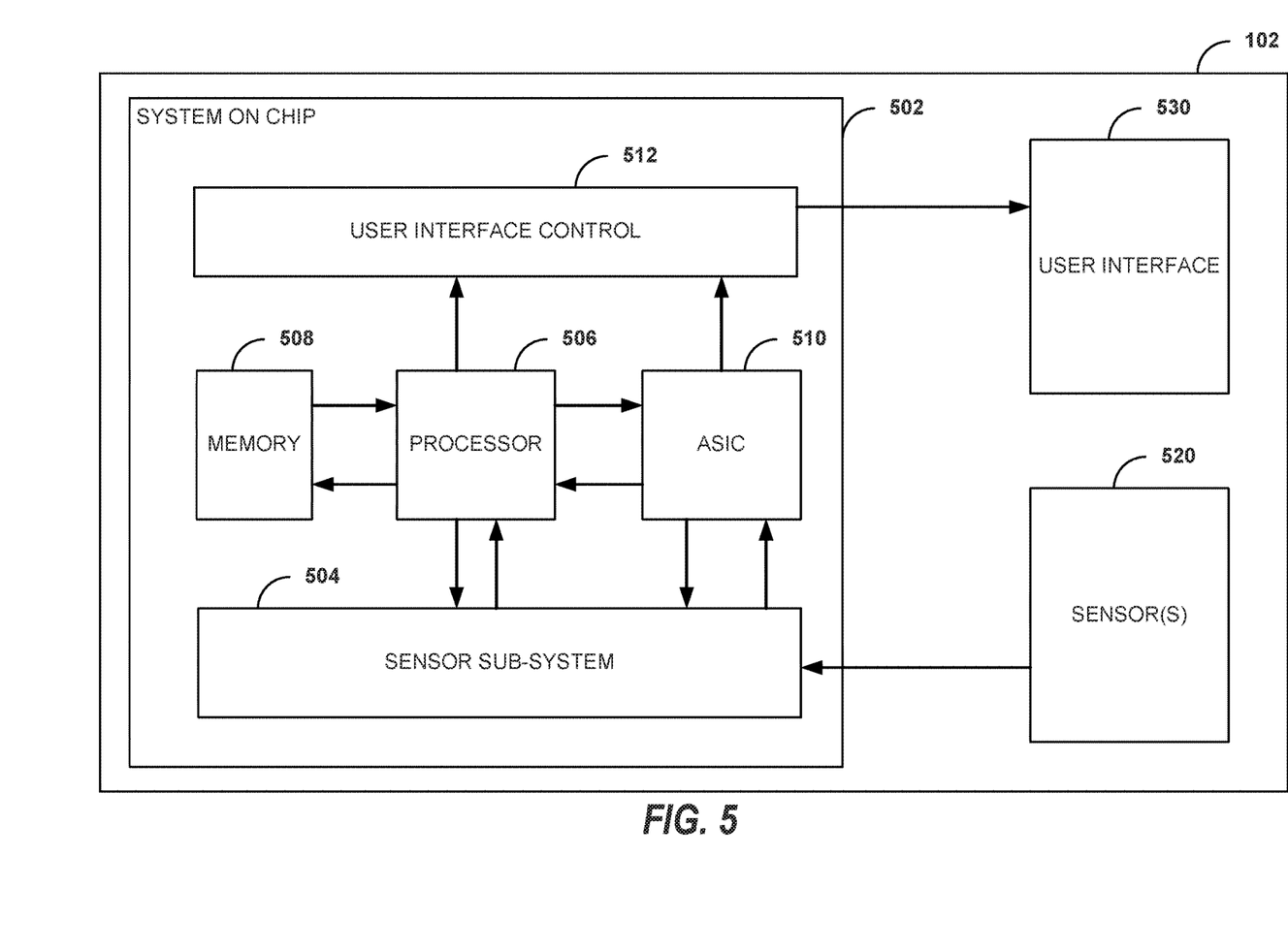
FIG. 5 illustrates an implementation of a wearable device whose settings may be optimized using machine learning, according to an example embodiment.

FIG. 5 illustrates an implementation of a wearable device 102 whose settings may be optimized using machine learning, according to an example embodiment. The wearable device 102 may include a system on a chip 502, one or more sensors 520, and a user interface 530.

The system on a chip 502 may include a sensor sub-system 504, a processor 506, a memory 508, an application-specific integrated circuit (ASIC) 510, and a user interface control 512. The sensor sub-system 504 may be generic and configurable for one or more use cases. The ASIC 510 may be a hardware implemented non-linear decision network that executes the algorithm trained by the cloud-based application 206.

The memory 508 may store a knowledge package 224; the knowledge package 224 may be accessed and executed by the processor 506. The execution of knowledge package 224 by the processor 506 may cause the processor 506 to provide instructions to the ASIC 510, receive results from the execution of the ASIC 510, and update the state of the machine learning algorithm by updating the memory 508.

The sensor(s) 520 may include one or more sensors to detect one or more of light, sound, pressure, humidity, acceleration, inertia, spatial orientation, heart rate, etc. The one or more sensor(s) 520 may enable one or more input modalities, such as tactile (touch), aural (sound), gestural (gestures), visual, etc., for providing input to the wearable device 102. The sensor-subsystem 504 may provide data sensed by one or more sensors 520 to the ASIC 510. The algorithm executed by the ASIC 510 may classify the data provided by the sensor sub-system 504 and determine one or more corresponding output modalities and output modality values to output in response to the provided data.

The user interface control 512 may receive input from the processor 506 and/or the ASIC 510, process the received input, generate a user output, and provide the generated user output to the user interface 530. The user interface 530 may include one or more of a display to present optical information, a speaker to generate aural information, a motor to generate vibrations, etc.

Figure 6:
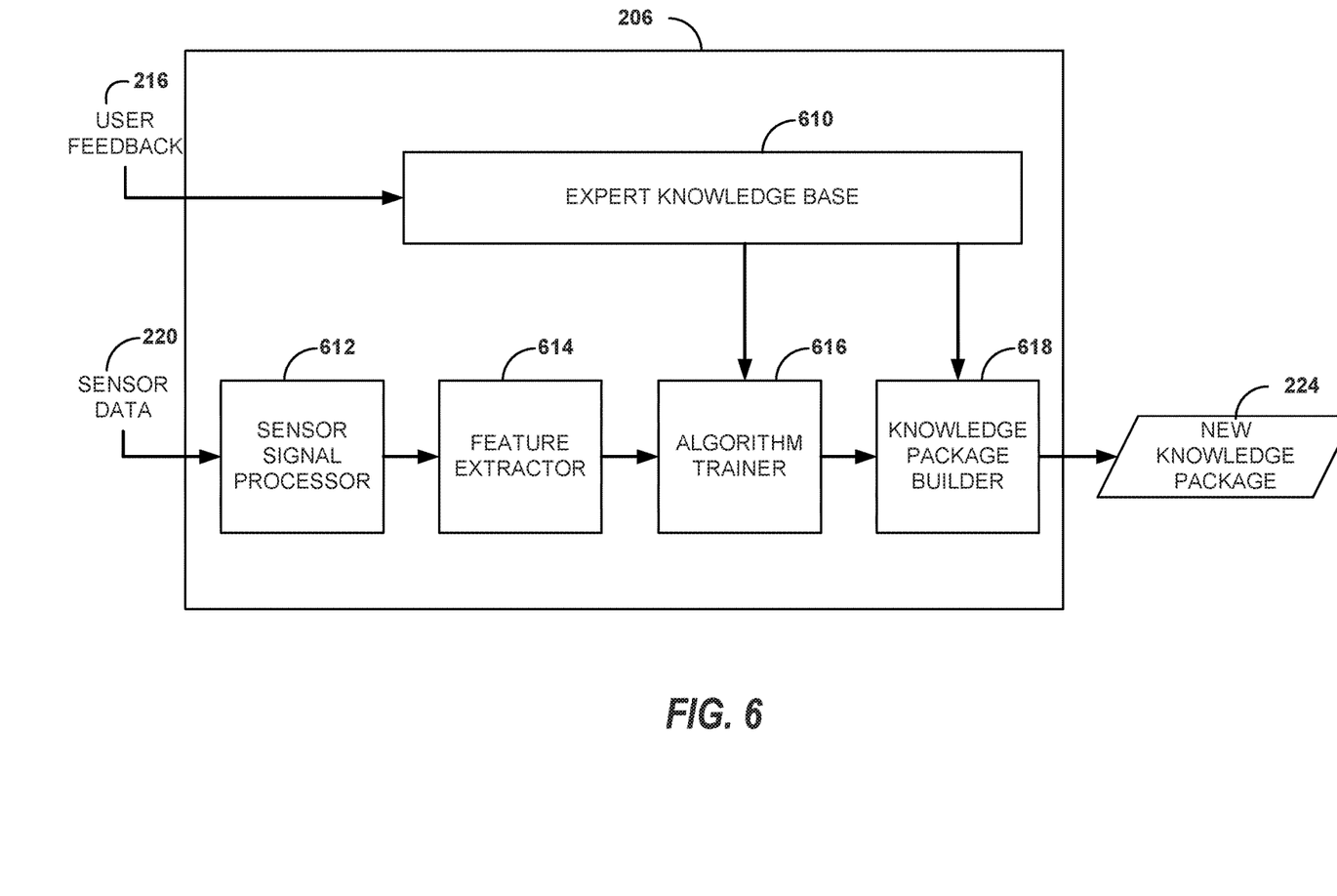
FIG. 6 is a data and control flow diagram illustrating operations of a cloud-based application for optimizing wearable device settings using machine learning, according to an example embodiment.

FIG. 6 is a data and control flow diagram 600 illustrating operations of a cloud-based application 206 for optimizing the settings of a wearable device 102 using machine learning, according to an example embodiment. The cloud-based application 206 may include an expert knowledge base 610, which represents domain knowledge for a domain in which the wearable device 102 is used (e.g., medical diagnostics/therapy, athletics, everyday use, etc.) The user feedback 216 sent to the cloud-based application 206 may be provided to the expert knowledge base 610.

The sensor data 220 sent to the cloud-based application 206 may be provided to a sensor signal processor 612, which may use signal processing techniques to analyze the sensor data 220.

The sensor signal processor 612 may provide the analyzed sensor data to a feature extractor 614, which may extract pertinent features from the analyzed sensor data.

The feature extractor 614 may provide the extracted features to an algorithm trainer 616. The algorithm trainer 616 may also receive the user feedback 216 and/or expert knowledge from the expert knowledge base 610. The algorithm trainer 616 may train a machine learning algorithm (e.g., a model of a neural network) that is to execute on the wearable device 102. The machine learning algorithm may attempt to simulate reactions of the user 202 wearing the wearable device 102 to various output modality values generated by the wearable device 102, and may attempt to adjust future output modality values based on the simulated reactions.

The algorithm trainer 616 may provide the trained machine learning algorithm to a knowledge package builder 618, which may incorporate the trained machine learning algorithm and information from the expert knowledge base 610 to build a new knowledge package 224. The cloud-based application 206 may send this new knowledge package 224 to the wearable device 102 for installation.

After the initial training and installation of the knowledge package 224, the user 202 may proceed to use the wearable device 102 normally (e.g., for its intended purpose(s)). As the user 202 uses the wearable device 102, the wearable device 102 may continue to collect sensor data corresponding to reactions of the user 202 in response to one or more output modalities 210 of the wearable device 102. The wearable device 102 may periodically send this collected sensor data to the cloud-based application 206. In response to receiving and analyzing the collected sensor data, the cloud-based application 206 may instruct the wearable device 102 to prompt the user 202 to initiate a subsequent training session similar to the initial training session 300 illustrated in FIG. 3. In an embodiment, the cloud-based application 206 may use the collected sensor data received from the wearable device 102 to generate a new knowledge package 224 using the operations illustrated in FIG. 6; in such an embodiment, the cloud-based application 206 may instruct the wearable device 102 to prompt the user 202 to install or download and install the new knowledge package 224.

Figure 7:
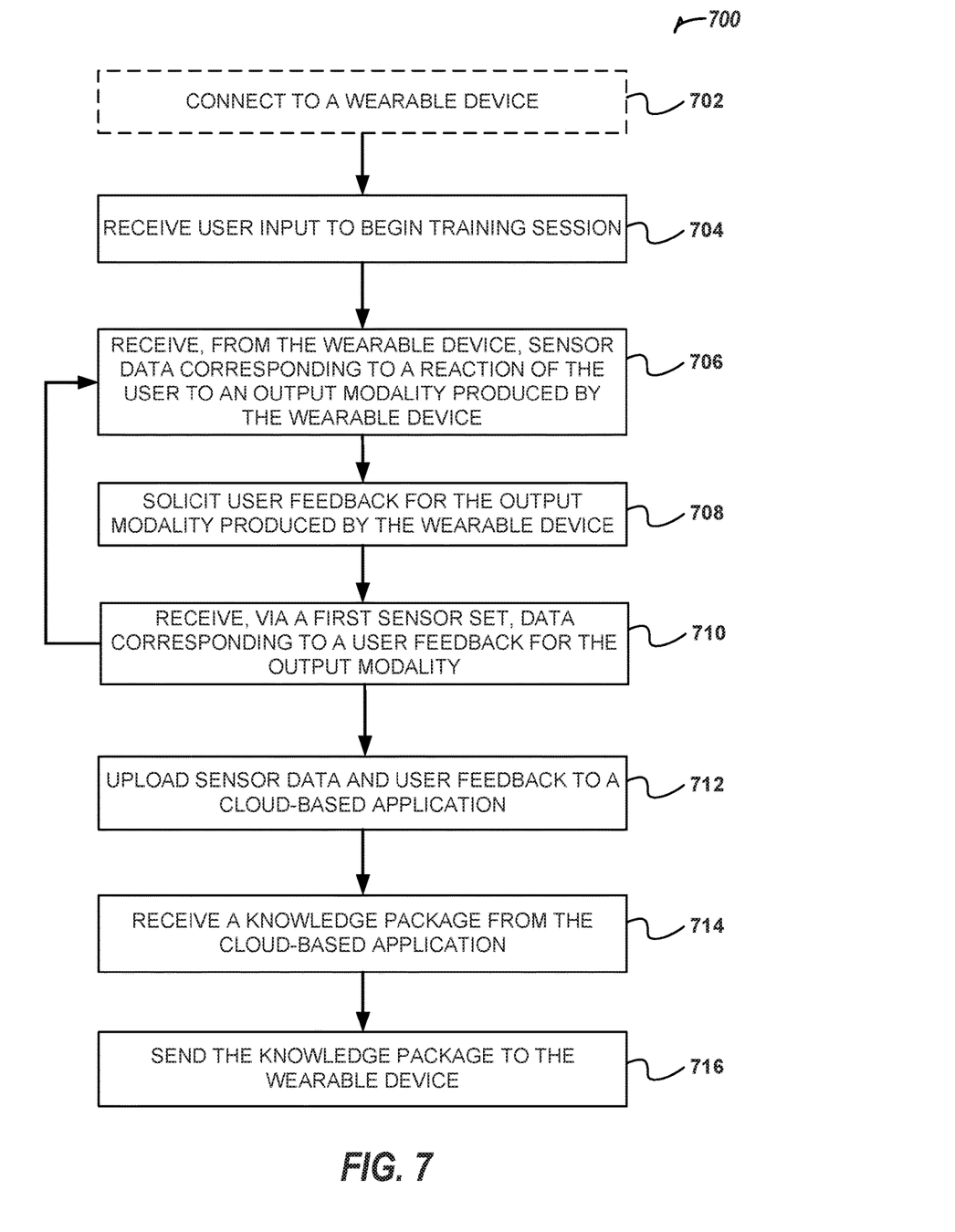
FIG. 7 illustrates a method executed by a mobile device for optimizing wearable device settings using machine learning, according to an example embodiment.

FIG. 7 illustrates a method 700 executed by a mobile device for optimizing wearable device settings using machine learning, according to an example embodiment. In method 700, a mobile device 204 is used to collect user feedback on behalf of the wearable device 102.

If the mobile device 204 is not yet connected to the wearable device 102, the mobile device 204 connects to the wearable device 102 (operation 702).

User input to begin the training session is received by the mobile device 204 (operation 704).

Sensor data corresponding to a reaction of the user to an output modality produced by the wearable device is received (operation 706).

User feedback for the output modality produced by the wearable device is solicited (operation 708).

Data corresponding to a user feedback for the output modality is received via a first sensor set (operation 710).

Operations 706-710 may be repeated if multiple modalities are output by the wearable device 102 and/or if multiple iterations of a single output modality are performed.

The sensor data and user feedback data are uploaded to a cloud-based application (operation 712).

A knowledge package is received from the cloud-based application (operation 714).

The knowledge package is sent to the wearable device (operation 716).

Figure 8:
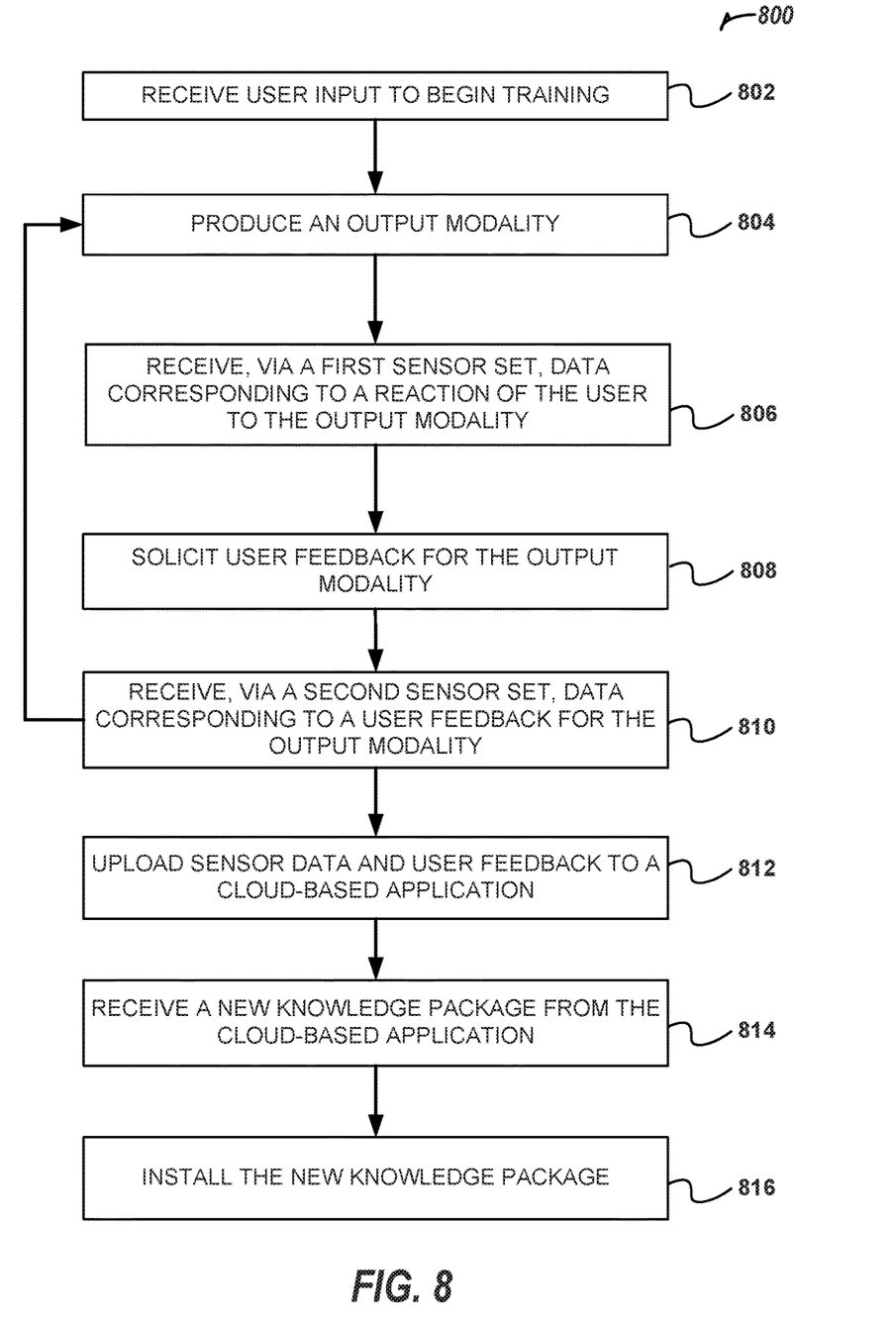
FIG. 8 illustrates a method executed by a wearable device for optimizing wearable device settings using machine learning, according to an example embodiment.

FIG. 8 illustrates a method 800 executed by a wearable device for optimizing wearable device settings using machine learning, according to an example embodiment. In method 800, only the wearable device 102 is used; a mobile device 204 is not used.

User input to begin the training session is received by the wearable device 102 (operation 804).

An output modality is produced by the wearable device 102 (operation 804).

Data corresponding to a reaction of the user to the output modality is received via a first sensor set of the wearable device 102 (operation 806).

User feedback for the output modality is solicited from the user by the wearable device 102 (operation 808).

Data corresponding to a user feedback for the output modality is received via a second sensor set of the wearable device 102 (operation 810).

Operations 804-810 may be repeated if multiple modalities are output by the wearable device 102 and/or if multiple iterations of a single output modality are performed.

The sensor data and user feedback data are uploaded to a cloud-based application (operation 812).

A knowledge package is received from the cloud-based application (operation 814).

The knowledge package is installed by the wearable device 102 (operation 816).

Figure 9:
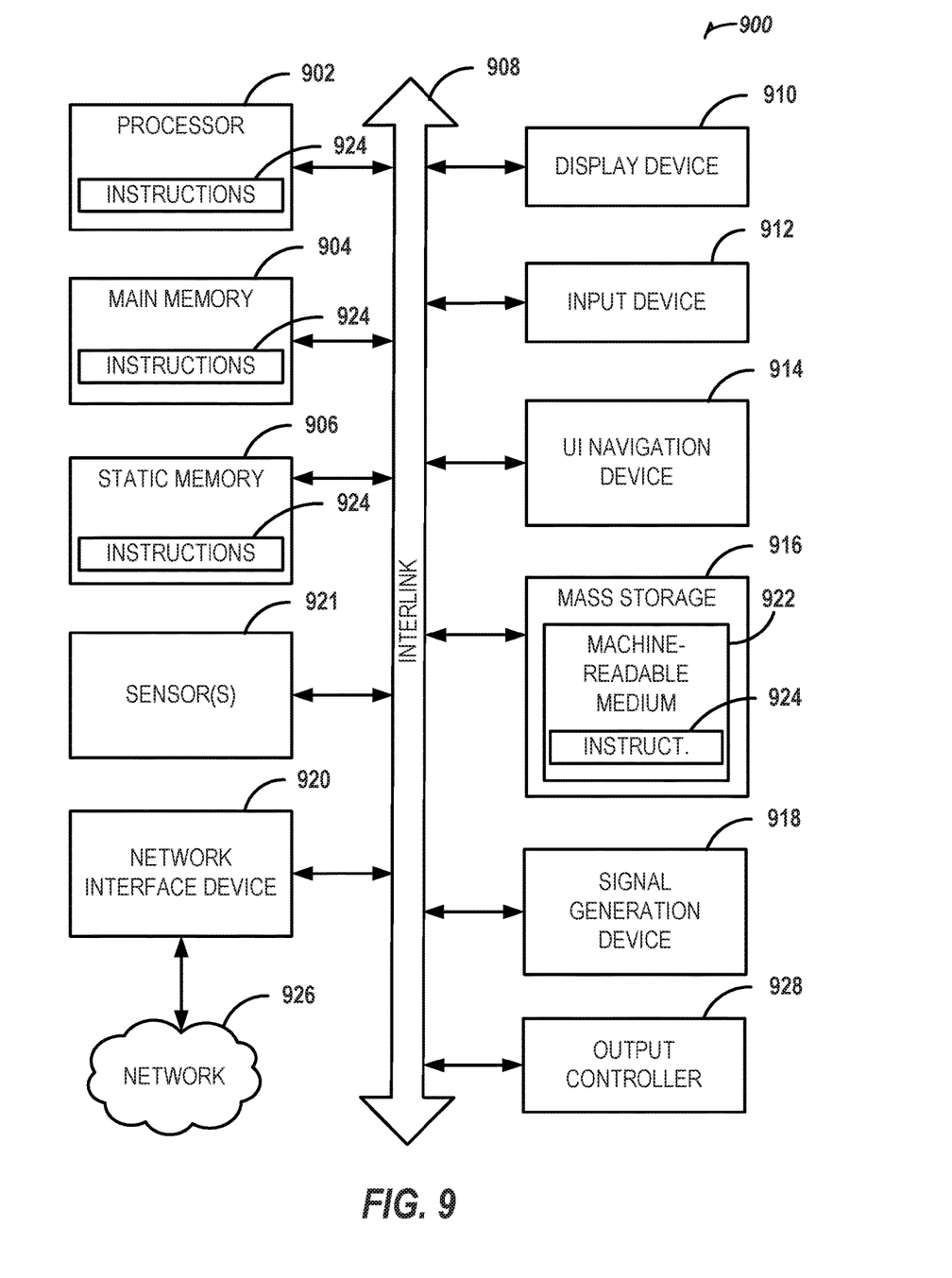
FIG. 9 is a block diagram illustrating an example of a machine, upon which any one or more example embodiments may be implemented.

FIG. 9 is a block diagram illustrating an example of a machine 900, upon which any one or more example embodiments may be implemented. In alternative embodiments, the machine 900 may operate as a standalone device or may be connected (e.g., networked) to other machines. In a networked deployment, the machine 900 may operate in the capacity of a server machine, a client machine, or both in a client-server network environment. In an example, the machine 900 may act as a peer machine in a peer-to-peer (P2P) (or other distributed) network environment. The machine 900 may implement or include any portion of the systems, devices, or methods illustrated in FIGS. 1-8, and may be a computer, a server, or any machine capable of executing instructions (sequential or otherwise) that specify actions to be taken by that machine. Further, although only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations, etc.

Examples, as described herein, may include, or may operate by, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910, an alphanumeric input device 912 (e.g., a keyboard), and a user interface (UI) navigation device 914 (e.g., a mouse). In an example, the display unit 910, input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensor. The machine 900 may include an output controller 928, such as a serial (e.g., USB, parallel, or other wired or wireless (e.g., infrared (IR), near field communication (NFC), etc.) connection to communicate or control one or more peripheral devices (e.g., a printer, card reader, etc.)

The storage device 916 may include a machine-readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine-readable media.

Although the machine-readable medium 922 is illustrated as a single medium, the term "machine-readable medium" may include a single medium or multiple media (e.g., a centralized or distributed database, and/or associated caches and servers) configured to store the one or more instructions 924.

The term "machine-readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples may include solid-state memories, and optical and magnetic media. Accordingly, machine-readable media are not transitory propagating signals. Specific examples of machine-readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks.

The instructions 924 may further be transmitted or received over a communications network 926 using a transmission medium via the network interface device 920 utilizing any one of a number of transfer protocols (e.g., frame relay, Internet protocol (IP), transmission control protocol (TCP), user datagram protocol (UDP), hypertext transfer protocol (HTTP), Message Queuing Telemetry Transport (MQTT), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMAX®), IEEE 802.15.4 family of standards, Bluetooth®, Bluetooth® low energy technology, ZigBee®, peer-to-peer (P2P) networks, among others. In an example, the network interface device 920 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

ADDITIONAL NOTES & EXAMPLE EMBODIMENTS

Example 1 is an apparatus for optimizing wearable device settings using machine learning, the apparatus comprising: a processor coupled to a sensor set of a wearable device; a user interface control to control a user interface of the wearable device, the user interface including an output mechanism capable of producing an output modality; and an integrated circuit (IC) coupled to the processor, the IC to execute a classification algorithm trained by a cloud-based application using a machine learning algorithm, the classification algorithm to: classify sensor data detected by a sensor of the sensor set; and determine an output modality value based at least partially on the classified sensor data.

In Example 2, the subject matter of Example 1 optionally includes wherein the sensor is one of: an accelerometer, a gyrometer, an inclinometer, a barometer, a thermometer, a microphone, a heart rate sensor, a compass, or a hygrometer.

In Example 3, the subject matter of any one or more of Examples 1-2 optionally include wherein the user interface includes at least one of: a light display to generate light, a speaker to generate sound, and a motor to cause the wearable device to vibrate.

In Example 4, the subject matter of any one or more of Examples 1-3 optionally include wherein the wearable device is a wristwatch.

In Example 5, the subject matter of any one or more of Examples 1-4 optionally include wherein the classification algorithm is trained by the cloud-based application in response to a training session, the training session including a modality interaction session, the modality interaction session to include the steps of: the wearable device to produce an output corresponding to an output modality; a sensor of the sensor set to detect sensor data corresponding to an action produced by a user of the wearable device in response to the produced output; a prompt of the user for feedback regarding the produced output; and receipt of a response to the feedback prompt; wherein the cloud-based application is to receive the detected sensor data and the feedback response; and wherein the cloud-based application is to produce a knowledge package, the knowledge package to include the trained classification algorithm.

In Example 6, the subject matter of Example 5 optionally includes wherein an output mechanism of a mobile device separate and distinct from the wearable device is to present a feedback prompt to the user; and wherein an input mechanism of the mobile device is to receive a response to the feedback prompt.

In Example 7, the subject matter of Example 6 optionally includes wherein the input mechanism of the mobile device is at least one of: tactile input, aural input, gesture input, facial input, movement of the mobile device, free-form text input, and selection of an emoji.

In Example 8, the subject matter of any one or more of Examples 5-7 optionally include wherein the cloud-based application is to transmit the trained classification algorithm to the mobile device; and wherein the mobile device is to transmit the trained classification algorithm to the wearable device.

In Example 9, the subject matter of any one or more of Examples 5-8 optionally include wherein the apparatus is to update itself by installation of the trained classification algorithm into the apparatus.

In Example 10, the subject matter of any one or more of Examples 6-9 optionally include wherein the mobile device is a smartphone.

In Example 11, the subject matter of any one or more of Examples 6-10 optionally include wherein the mobile device is a tablet computer.

In Example 12, the subject matter of any one or more of Examples 6-11 optionally include wherein the mobile device is a notebook computer.

Example 13 is a method for optimizing settings of a wearable device using machine learning, the method comprising: receiving, from a wearable device, sensor data corresponding to a reaction of a user wearing the wearable device to an output modality produced by the wearable device; soliciting user feedback for the output modality produced by the wearable device; receiving user feedback data corresponding to a user feedback for the output modality; uploading the sensor data and the user feedback data to a cloud-based application; receiving a knowledge package, including a classification algorithm trained using the sensor data and the user feedback data, from the cloud-based application; and sending the knowledge package to the wearable device.

In Example 14, the subject matter of Example 13 optionally includes wherein soliciting user feedback is performed by an output mechanism of a mobile device separate and distinct from the wearable device; and wherein receiving user feedback data is performed by an input mechanism of the mobile device.

In Example 15, the subject matter of any one or more of Examples 13-14 optionally include wherein the user feedback data includes at least one of: tactile input, aural input, gesture input, facial input, movement of the mobile device, free-form text input, and selection of an emoji.

In Example 16, the subject matter of any one or more of Examples 13-15 optionally include the wearable device installing the knowledge package.

In Example 17, the subject matter of any one or more of Examples 13-16 optionally include wherein the output modality produced by the wearable device is one of: light generated by a light display, sound generated by a speaker, or vibrations generated by a motor.

In Example 18, the subject matter of any one or more of Examples 13-17 optionally include wherein the sensor data is produced by at least one of: an accelerometer, a gyrometer, an inclinometer, a barometer, a thermometer, a microphone, a heart rate sensor, a compass, and a hygrometer.

In Example 19, the subject matter of any one or more of Examples 13-18 optionally include wherein the wearable device is a wristwatch.

In Example 20, the subject matter of any one or more of Examples 13-19 optionally include wherein the mobile device is a smartphone.

In Example 21, the subject matter of any one or more of Examples 13-20 optionally include wherein the mobile device is a tablet computer.

In Example 22, the subject matter of any one or more of Examples 13-21 optionally include wherein the mobile device is a notebook computer.

Example 23 is a method for optimizing settings of a wearable device using machine learning, the method comprising: producing an output modality having one of a plurality of output modality values; receiving, via a sensor set, sensor data corresponding to a reaction of a user to the output modality, the user wearing the wearable device; soliciting user feedback for the output modality; receiving, via an input mechanism of the wearable device, user feedback data corresponding to a user feedback for the output modality; uploading the sensor data and the user feedback data to a cloud-based application; and receiving a knowledge package, including a classification algorithm trained using the sensor data and the user feedback data, from the cloud-based application.

In Example 24, the subject matter of Example 23 optionally includes wherein the output modality produced by the wearable device is one of: light generated by a light display, sound generated by a speaker, or vibrations generated by a motor.

In Example 25, the subject matter of any one or more of Examples 23-24 optionally include wherein the user feedback data includes at least one of: tactile input, aural input, gesture input, facial input, movement of the mobile device, free-form text input, and selection of an emoji.

In Example 26, the subject matter of any one or more of Examples 23-25 optionally include the wearable device installing the knowledge package.

In Example 27, the subject matter of any one or more of Examples 23-26 optionally include wherein the sensor set includes at least one of: an accelerometer, a gyrometer, an inclinometer, a barometer, a thermometer, a microphone, a heart rate sensor, a compass, and a hygrometer.

In Example 28, the subject matter of any one or more of Examples 23-27 optionally include wherein the wearable device is a wristwatch.

Example 29 is at least one machine-readable medium including instructions that, when executed by a machine, cause the machine to perform operations of any of the methods of Examples 13-28.

Example 30 is an apparatus comprising means for performing any of the methods of Examples 13-28.

Example 31 is an apparatus for optimizing settings of a wearable device using machine learning, the apparatus comprising: means for receiving, from a wearable device, sensor data corresponding to a reaction of a user wearing the wearable device to an output modality produced by the wearable device; means for soliciting user feedback for the output modality produced by the wearable device; means for receiving user feedback data corresponding to a user feedback for the output modality; means for uploading the sensor data and the user feedback data to a cloud-based application; means for receiving a knowledge package, including a classification algorithm trained using the sensor data and the user feedback data, from the cloud-based application; and means for sending the knowledge package to the wearable device.

In Example 32, the subject matter of Example 31 optionally includes wherein soliciting user feedback is performed by an output means of a mobile device separate and distinct from the wearable device; and wherein receiving user feedback data is performed by an input means of the mobile device.

In Example 33, the subject matter of any one or more of Examples 31-32 optionally include wherein the user feedback data includes at least one of: tactile input, aural input, gesture input, facial input, movement of the mobile device, free-form text input, and selection of an emoji.

In Example 34, the subject matter of any one or more of Examples 31-33 optionally include wherein the wearable device is to install the knowledge package.

In Example 35, the subject matter of any one or more of Examples 31-34 optionally include wherein the output modality produced by the wearable device is one of: light generated by a light generating means, sound generated by a sound generating means, or vibrations generated by a vibrating means.

In Example 36, the subject matter of any one or more of Examples 31-35 optionally include wherein the sensor data is produced by at least one of: an accelerometer, a gyrometer, an inclinometer, a barometer, a thermometer, a microphone, a heart rate sensor, a compass, and a hygrometer.

In Example 37, the subject matter of any one or more of Examples 31-36 optionally include wherein the wearable device is a wristwatch.

In Example 38, the subject matter of any one or more of Examples 31-37 optionally include wherein the mobile device is a smartphone.

In Example 39, the subject matter of any one or more of Examples 31-38 optionally include wherein the mobile device is a tablet computer.

In Example 40, the subject matter of any one or more of Examples 31-39 optionally include wherein the mobile device is a notebook computer.

Example 41 is an apparatus for optimizing settings of a wearable device using machine learning, the apparatus comprising: means for producing an output modality having one of a plurality of output modality values; means for receiving sensor data corresponding to a reaction of a user to the output modality, the user wearing the wearable device; means for soliciting user feedback for the output modality; means for receiving user feedback data corresponding to a user feedback for the output modality; means for uploading the sensor data and the user feedback data to a cloud-based application; and means for receiving a knowledge package, including a classification algorithm trained using the sensor data and the user feedback data, from the cloud-based application.

In Example 42, the subject matter of Example 41 optionally includes wherein the output modality produced by the wearable device is one of: light generated by a light generating means, sound generated by a sound generating means, or vibrations generated by a vibrating means.

In Example 43, the subject matter of any one or more of Examples 41-42 optionally include wherein the user feedback data includes at least one of: tactile input, aural input, gesture input, facial input, movement of the mobile device, free-form text input, and selection of an emoji.

In Example 44, the subject matter of any one or more of Examples 41-43 optionally include the wearable device installing the knowledge package.

In Example 45, the subject matter of any one or more of Examples 41-44 optionally include wherein the sensor data was produced by at least one of: an accelerometer, a gyrometer, an inclinometer, a barometer, a thermometer, a microphone, a heart rate sensor, a compass, and a hygrometer.

In Example 46, the subject matter of any one or more of Examples 41-45 optionally include wherein the wearable device is a wristwatch.

Each of these non-limiting examples can stand on its own, or can be combined in various permutations or combinations with one or more of the other examples.

Conventional terms in the fields of computer systems and wearable devices have been used herein. The terms are known in the art and are provided only as a non-limiting example for convenience purposes. Accordingly, the interpretation of the corresponding terms in the claims, unless stated otherwise, is not limited to any particular definition.

Although specific embodiments have been illustrated and described herein, it will be appreciated by those of ordinary skill in the art that any arrangement that is calculated to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. Moreover, in the following claims, the terms "first," "second," and "third," etc. are used merely as labels, and are not intended to impose numerical requirements on their objects. In this document, a sensor set may include one or more sensors, which may be of different types. Furthermore, two different sensor sets may include one or more sensors that belong to both sensor sets.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments may be combined with each other in various combinations or permutations. The scope of the embodiments should be determined with reference to the appended claims, along with the full scope of equivalents to which such claims are entitled.

The above description is intended to be illustrative, and not restrictive. For example, the above-described examples (or one or more aspects thereof) may be used in combination with each other. Other embodiments may be used, such as by one of ordinary skill in the art upon reviewing the above description.

What is claimed is:

1. An apparatus for optimizing wearable device settings using machine learning, the apparatus comprising:
   a processor coupled to a sensor set of a wearable device;
   a user interface control to control a user interface of the wearable device, the user interface including an output mechanism capable of producing an output modality; and
   an integrated circuit (IC) coupled to the processor, the IC to execute a classification algorithm trained by a cloud-based application using a machine learning algorithm, the classification algorithm to:
   classify sensor data detected by a sensor of the sensor set; and
   determine an output modality value based at least partially on the classified sensor data.

2. The apparatus of claim 1, wherein the sensor is one of: an accelerometer, a gyrometer, an inclinometer, a barometer, a thermometer, a microphone, a heart rate sensor, a compass, or a hygrometer.

3. The apparatus of claim 1, wherein the user interface includes at least one of:
   a light display to generate light, a speaker to generate sound, and a motor to cause the wearable device to vibrate.

4. The apparatus of claim 1, wherein the wearable device is a wristwatch.

5. The apparatus of claim 1, wherein the classification algorithm is trained by the cloud-based application in response to a training session, the training session including a modality interaction session, the modality interaction session to include the steps of:

the wearable device to produce an output corresponding to an output modality;
a sensor of the sensor set to detect sensor data corresponding to an action produced by a user of the wearable device in response to the produced output;
a prompt of the user for feedback regarding the produced output; and
receipt of a response to the feedback prompt;
wherein the cloud-based application is to receive the detected sensor data and the feedback response; and
wherein the cloud-based application is to produce a knowledge package, the knowledge package to include the trained classification algorithm.

6. The apparatus of claim 5, wherein an output mechanism of a mobile device separate and distinct from the wearable device is to present a feedback prompt to the user; and
wherein an input mechanism of the mobile device is to receive a response to the feedback prompt.

7. The apparatus of claim 6, wherein the input mechanism of the mobile device is at least one of:
tactile input, aural input, gesture input, facial input, movement of the mobile device, free-form text input, and selection of an emoji.

8. The apparatus of claim 5, wherein the cloud-based application is to transmit the trained classification algorithm to the mobile device; and
wherein the mobile device is to transmit the trained classification algorithm to the wearable device.

9. The apparatus of claim 5, wherein the apparatus is to update itself by installation of the trained classification algorithm into the apparatus.

10. A method for optimizing settings of a wearable device using machine learning, the method comprising:
receiving, from a wearable device, sensor data corresponding to a reaction of a user wearing the wearable device to an output modality produced by the wearable device;
soliciting user feedback for the output modality produced by the wearable device;
receiving user feedback data corresponding to a user feedback for the output modality;
uploading the sensor data and the user feedback data to a cloud-based application;
receiving a knowledge package, including a classification algorithm trained using the sensor data and the user feedback data, from the cloud-based application; and
sending the knowledge package to the wearable device.

11. The method of claim 10, wherein soliciting user feedback is performed by an output mechanism of a mobile device separate and distinct from the wearable device; and
wherein receiving user feedback data is performed by an input mechanism of the mobile device.

12. The method of claim 10, wherein the user feedback data includes at least one of:
tactile input, aural input, gesture input, facial input, movement of the mobile device, free-form text input, and selection of an emoji.

13. The method of claim 10, wherein the output modality produced by the wearable device is one of:
light generated by a light display, sound generated by a speaker, or vibrations generated by a motor.

14. The method of claim 10, wherein the sensor data is produced by at least one of:
an accelerometer, a gyrometer, an inclinometer, a barometer, a thermometer, a microphone, a heart rate sensor, a compass, and a hygrometer.

15. At least one non-transitory machine-readable medium including instructions that, when executed by a machine, cause the machine to:
receive, from a wearable device, sensor data corresponding to a reaction of a user to an output modality produced by the wearable device, the user wearing the wearable device;
solicit user feedback for the output modality produced by the wearable device;
receive user feedback data corresponding to a user feedback for the output modality;
upload the sensor data and the user feedback data to a cloud-based application;
receive a knowledge package, including a classification algorithm trained using the sensor data and the user feedback data, from the cloud-based application; and
send the knowledge package to the wearable device.

16. The at least one non-transitory machine-readable medium of claim 15, wherein to solicit user feedback is performed by an output mechanism of a mobile device separate and distinct from the wearable device; and
wherein to receive user feedback data is performed by an input mechanism of the mobile device.

17. The at least one non-transitory machine-readable medium of claim 15, wherein the user feedback data includes at least one of:
tactile input, aural input, gesture input, facial input, movement of the mobile device, free-form text input, and selection of an emoji.

18. The at least one non-transitory machine-readable medium of claim 15, wherein the output modality produced by the wearable device is one of:
light generated by a light display, sound generated by a speaker, or vibrations generated by a motor.

19. The at least one non-transitory machine-readable medium of claim 15, wherein the sensor data is produced by at least one of:
an accelerometer, a gyrometer, an inclinometer, a barometer, a thermometer, a microphone, a heart rate sensor, a compass, and a hygrometer.

20. At least one non-transitory machine-readable medium including instructions that, when executed by a machine, cause the machine to:
produce an output modality having one of a plurality of output modality values;
receive, via a sensor set, sensor data corresponding to a reaction of a user to the output modality, the user wearing the wearable device;
solicit user feedback for the output modality;
receive, via an input mechanism of the wearable device, user feedback data corresponding to a user feedback for the output modality;
upload the sensor data and the user feedback data to a cloud-based application; and
receive a knowledge package, including a classification algorithm trained using the sensor data and the user feedback data, from the cloud-based application.

21. The at least one non-transitory machine-readable medium of claim 20, wherein the output modality produced by the wearable device is one of:
light generated by a light display, sound generated by a speaker, or vibrations generated by a motor.

22. The at least one non-transitory machine-readable medium of claim 20, wherein the user feedback data includes at least one of:

tactile input, aural input, gesture input, facial input, movement of the mobile device, free-form text input, and selection of an emoji.

23. The at least one non-transitory machine-readable medium of claim 20, wherein the sensor set includes at least one of:

an accelerometer, a gyrometer, an inclinometer, a barometer, a thermometer, a microphone, a heart rate sensor, a compass, and a hygrometer.

24. The at least one non-transitory machine-readable medium of claim 20, wherein the wearable device is a wristwatch.

* * * * *